United States Patent
Carlstrom et al.

(10) Patent No.: US 6,920,779 B2
(45) Date of Patent: Jul. 26, 2005

(54) METHOD OF ESTIMATING ENGINE LUBRICANT CONDITION

(75) Inventors: Kevin R. Carlstrom, Fort Wayne, IN (US); Gerald L. Larson, Fort Wayne, IN (US); Frank Bondarowicz, Park Ridge, IL (US)

(73) Assignee: International Truck Intellectual Property Company, LLC, Warrenville, IL (US)

( * ) Notice: Subject to any disclaimer, the term of this patent is extended or adjusted under 35 U.S.C. 154(b) by 322 days.

(21) Appl. No.: 10/295,360

(22) Filed: Nov. 15, 2002

(65) Prior Publication Data

US 2004/0093931 A1 May 20, 2004

(51) Int. Cl.[7] .............................................. G01M 15/00
(52) U.S. Cl. .................. 73/53.05; 73/117.3; 340/457.4
(58) Field of Search ............... 73/117.3, 53.05; 701/29–31, 101, 1; 340/438, 457.4

(56) References Cited

U.S. PATENT DOCUMENTS

| | | | |
|---|---|---|---|
| 4,082,511 A | * | 4/1978 | Bedford ........................ 436/60 |
| 4,383,931 A | | 5/1983 | Ryu et al. |
| 5,604,441 A | | 2/1997 | Freese, V et al. |
| 5,750,887 A | | 5/1998 | Schricker |
| 5,800,782 A | | 9/1998 | Hagstrom et al. |
| 5,914,890 A | | 6/1999 | Sarangapani et al. |
| 5,987,976 A | | 11/1999 | Sarangapani |
| 6,004,910 A | | 12/1999 | Bloch et al. |
| 6,162,769 A | | 12/2000 | Polhaar et al. |
| 6,253,601 B1 | | 7/2001 | Wang et al. |
| 6,423,670 B2 | | 7/2002 | Locke et al. |

* cited by examiner

*Primary Examiner*—Robert Raevis
(74) *Attorney, Agent, or Firm*—Jeffrey P. Calfa; Dennis Kelly Sullivan; Susan L. Lukasik

(57) ABSTRACT

A motor vehicle having an internal combustion engine and a lubricating oil circulation system provides estimates of the distance remaining before an oil change becomes imperative. An indirect estimate of the depletion of various additives and the deterioration of oil operating characteristics is based on engine operating variables including oil temperature, ignition timing and engine load. The limit of depletion of total base number is dynamic, since it is set against total acid number and the two figures are independently calculated.

12 Claims, 8 Drawing Sheets

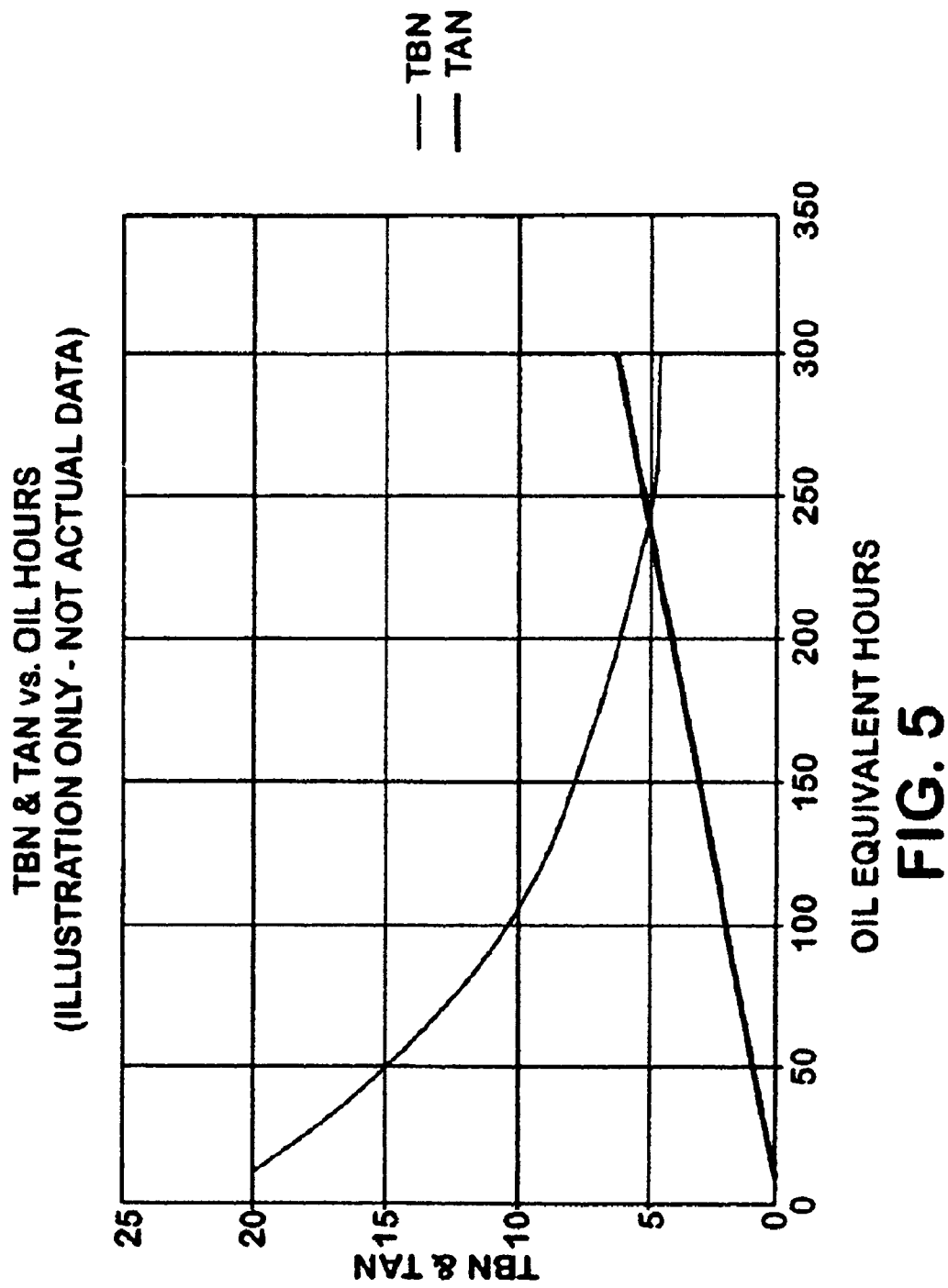

METHOD OF ESTIMATING ENGINE LUBRICANT CONDITION

BACKGROUND OF THE INVENTION

1. Field of the Invention

The present invention relates generally to a method for estimating the condition of engine lubricating oil in situ, and more particularly to a method of monitoring engine operating variables for predicting economically optimal oil change intervals.

2. Description of the Prior Art

Truck fleet operation is highly competitive and fleet operators are highly conscious of the need to balance preventive maintenance costs, repair costs, fleet operational availability and vehicle replacement costs. While cost effective fleet management and readiness requirements demand the practice of preventive maintenance, one aspect of preventive maintenance, the engine lubricating oil change interval, has often been conservatively biased based on an assumption that the vehicle has been exposed to severe service and that the lubricating oil is thus likely to have a short useful life. Changing lubricating oil costs money and removes a vehicle from service for a period of time. Increased vehicle down time may compel an operator to have more tractors in a fleet than would otherwise be necessary and high frequency maintenance complicates fleet scheduling. While changes of lubricating oil extend the service life of a vehicle they are economically productive only up to a point, and become wasteful and uneconomic if done excessively often.

Changes of engine lubricating oil are necessitated by the fact that lubricating oil deteriorates with use. With degradation of the quality of lubricating oil, an engine is exposed to unnecessary wear and corrosion. The degree, and character, of lubricating oil degradation is related to a number of engine operating variables. These include temperature cycling of the lubricant, exposure of the oil to excessively high temperature, engine operating loads, ambient conditions of operation (e.g. high altitude operation, dust, etc.), the number of cylinder combustion cycles, etc. The changes in various characteristic variables of the engine lubricating oil can be predicted as functions in these operating variables and accumulated vehicle running time. Included among the characteristic variables subject to change are oil viscosity, the accumulation of soot in the oil, the infiltration of foreign material into the oil, the quantity of alkaline buffers left in the oil per unit volume (measured in terms Total Base Number or TBN), the quantity of acidic species, some in the form of $H_2SO_4$, accumulating in the oil per unit volume (referred to as the Total Acid Number or TAN), and the depletion of special lubrication enhancing and anti-oxidant agents, such as zinc dithiophosphate and related oil-soluble salts, the quantity per unit volume of which are measured as an Active Zinc Number (AZN).

Any one or more of the variables relating to engine lubricating oil condition may be estimated as indicators of the oil's condition. The estimation of soot may be taken as an example. Soot is primarily a by-product of combustion of hydrocarbon fuels resulting from unburned or partially burned hydrocarbons as well as some ash, which can agglomerate into particles which damage an engine by wear. Soot moves from the cylinder to the engine oil as a result of cylinder blow-by or by adhesion to the cylinder walls from which it is swept by the piston rings into the oil. Soot becomes an issue in engine oil when the amount of soot overwhelms dispersants in the oil and begins to agglomerate. The transfer of soot from a cylinder to the engine oil varies with a number factors, such as the use of low volatility diesel fuel blends at low ambient temperatures or operation of the engine at a disadvantageous point on the engine torque curve. However, heavy soot loading of the oil stems primarily from high engine loads over extended periods of time. High loads result in increased cylinder blow-by Which adds soot to the oil at a greater rate and which produces localized high temperatures in the oil leading to molecular degradation. Engine load is not typically directly measured, but is closely related to the Brake Mean Effective Pressure (BMEP), with, $$\text{SOOT}=C_0 \int \text{BMEP } dn \text{ for } n=0 \text{ to } n=M \quad (1)$$

where $C_0$ is a proportionality constant and
n is engine revolutions.

However, BMEP is currently difficult and expensive to measure in real time engine applications. BMEP may in turn be estimated from fuel flow and engine speed allowing soot accumulated over a period of time to be calculated as follows, $$\text{SOOT}=C_0 \int M_f/n \text{ dt from } t=0 \text{ to } t=T \quad (2)$$

where $M_f$ is fuel flow,
t is time, and
n is engine revolutions.
$C_0$ is a proportionally constant Other products are produced in the combustion process which infiltrate into the lubricating oil and progressively degrade its performance. Sulfuric acid, $H_2SO_4$, and other sulfur compounds form from sulfur in the fuel and oxygen and water from the air. Once in the oil these compounds, particularly $H_2SO_4$, dissolve in any water they encounter and form a highly corrosive acid which attacks engine components. Engine oil additives, such as detergents, are designed to give water contaminants in the oil an elevated (i.e. basic) ph to neutralize $H_2SO_4$. The total concentration of these alkaline additives is measured in equivalents of mg of potassium hydroxide (KOH) per gram of water. The measurement is expressed as the total base number (TBN). $H_2SO_4$ infiltration will progressively deplete the TBN and will itself contribute to a progressively higher TAN.

Various additives can be provided to complement and prolong the inherent lubricity of the oil. Among these additives are various oil-soluble alkaline metal salts, including particularly zinc salts such as zinc dithiophosphate. The concentration of these additives is represented by an active zinc number (AZN).

Other factors are known to contribute to early oil degradation, particularly if engine duty cycles are of short duration. Water can contaminate engine oil from moisture bearing air entering through the oil filler nozzle or from the engine cooling system. If an engine does not reach or maintain a minimum threshold operating temperature, water which has contaminated the oil will not be forced by evaporation from the oil. As discussed above, water combines with the sulfur compound combustion by-products discussed above to form highly corrosive acids in the engine oil and thereby exposing an engine to corrosion damage.

Another possible engine contaminant is ethylene glycol, which can escape from the engine coolant system. Fuel contamination is also a possibility. Both of these contaminants reduce the lubricity of engine oil.

The estimation of the properties of the engine lubricating oil is most economically achieved if done using sensors commonly found on contemporaneous vehicles and without physical modification of engines. Existing sensors typically provide for measuring a variety of engine operating variables and while they indicate the conditions encountered by the oil they do not usually provide a direct indication of the condition of the oil. Among the operational variables commonly measured on diesel powered trucks are: crank shaft position, which can be used to generate a tachometer signal; ignition timing, which can be determined from crank shaft position and the timing of fuel injection; engine lubricating oil temperature; engine lubricating oil level; and fuel flow. Capacitance type engine oil level based sensors can provide one direct indication of oil condition, its dielectric constant. Contemporary diesel control provides for collecting the data by an on board computer such as an engine controller or an electrical system controller. These computers can be readily programmed to execute one or robust estimation functions based on the available data.

U.S. Pat. No. 6,253,601 to Wang, et al. and U.S. Pat. No. 5,750,887 to Schricker are examples of oil change interval estimation algorithms. The estimation functions developed by these references are stored as look up tables in the memory of on board computers. The functions are based on empirical data generated under controlled conditions with a given engine type and verified by direct analysis of the oil. Wang et al. disclose an estimation function based on measurements from an engine (oil) temperature sensor, a fueling rate meter, an engine speed sensor and what is termed an engine load sensor. Contrary to the statement in the patent, engine load appears not to be directly sensed, but estimated from the fuel flow rate and engine speed. From these values, estimates are generated for accumulated soot, TBN and oil viscosity. Schricker appears to monitor fuel to air ratios, engine speed, fuel injection timing. Brake mean effective pressure is derived as an indirect indication of engine load. Soot, oil oxidation, viscosity and TBN are estimated from the measured and calculated input variables. The accumulated values for the variables are compared to static limits to develop an oil change interval.

What is absent from the references is consideration of alternative properties of lubricating oil which may provide more accurate indications of the working life of the oil. The use of alternative properties may allow a more dynamic system than the static limits of the prior art and minimizes or eliminates physical changes to the engine provided for making the determination. Such a system could be used to implement a model of engine oil life which more effectively uses existing sensor data and on board data processing capability to optimize the oil change interval.

SUMMARY OF THE INVENTION

According to the invention there is provided a method for estimating the useful life of lubricating oil used in a motor vehicle's internal combustion engine. Total base number of the oil is taken as the prime limiting characteristic. Its minimum allowable level is set at the level where it equals the total acid number of the oil. Since the two estimates are independently calculated, the lower limit for TBN is subject to change depending upon observed operating conditions. The estimates are indirect being based on engine operating variables including oil temperature, ignition timing and engine load. The limit of depletion of total base number is dynamic, since it is set against total acid number and the two figures are independently calculated. The active zinc number is also estimated and compared to a minimum limit.

Additional effects, features and advantages will be apparent in the written description that follows.

BRIEF DESCRIPTION OF THE DRAWINGS

The novel features believed characteristic of the invention are set forth in the appended claims. The invention itself however, and preferred mode of use, further objects and advantages thereof, will best be understood by reference to the following detailed description of an illustrative embodiment when read in conjunction with the accompanying drawings, wherein:

FIG. 5 is a graph illustrating determination of the end of useful life for lubricating oil.

DETAILED DESCRIPTION OF THE INVENTION

Figure 1:
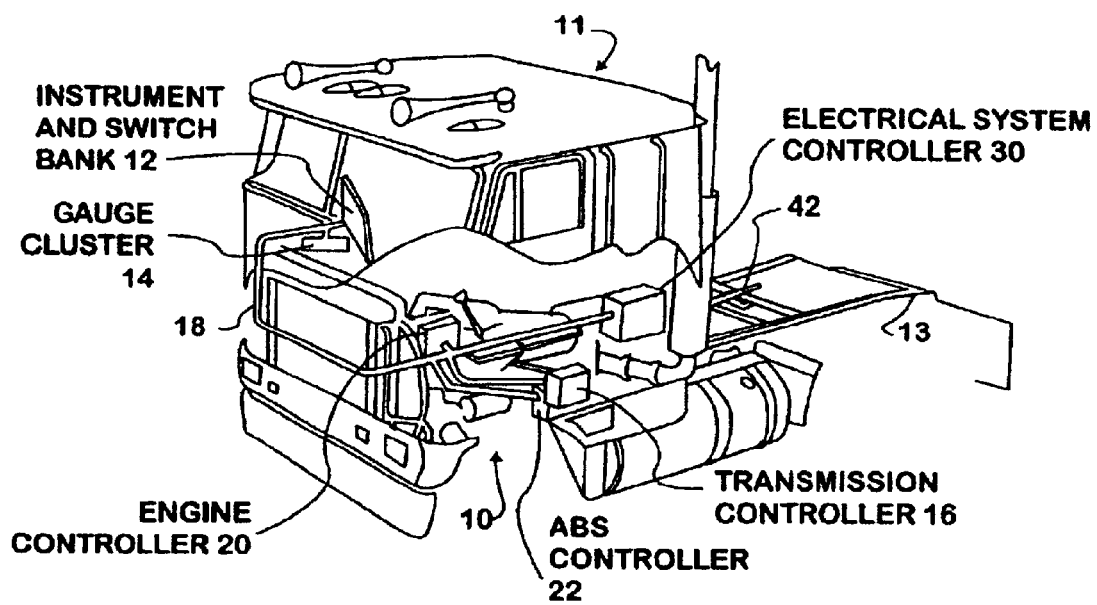
FIG. 1 is a perspective view in partial cutaway of a truck tractor incorporating an engine and a control network.

Referring now to the figures and more particularly to FIG. 1, a perspective view illustrates a vehicle 11 and an electrical control system 10 installed on the vehicle. Vehicle electrical system 10 comprises a twisted pair (either shielded or unshielded) cable operating as a serial data bus 18. One node of bus 18 is an electrical system controller (ESC) 30, which is a higher level data processing component of electrical control system 10. ESC 30 manages a number of vocational controllers connected to bus 18 as nodes and disposed on vehicle 11. Preferably, bus 18 and the various nodes attached thereto form a controller area network (CAN).

Active vehicle components are typically controlled by one of a group of autonomous, vocational controllers, which include a gauge cluster 14, an engine controller 20, which is typically supplied with an engine 19 (shown in FIG. 2), a transmission controller 16, an auxiliary instrument and switch bank 12, and an antilock brake system (ABS) controller 22. These vocational controllers are connected to ESC 30 over a serial data bus 18 as nodes. The autonomous vocational controllers include local data processing and programming and are typically supplied by the manufacturer of the controlled component. Bus 18 is typically a twisted pair cable constructed in accordance with SAE standard J1939. Although the autonomous vocational controllers handle many functions locally, they report data to ESC 30 and can receive operational requests from ESC 30.

ESC 30 may provide higher level data processing capable of implementing programmed, adaptive routines to improve operation of vehicle 11. Alternatively, these functions may be located in an on board computer which communicates with ESC 30 over bus 18. The present invention implements a model of lubricating oil useful life based on indirect sensor and engine telemetry as an oil life estimation algorithm preferably executed on ESC 30 or such an on board computer. It is possible to implement the algorithm on engine controller 20.

Figure 2:
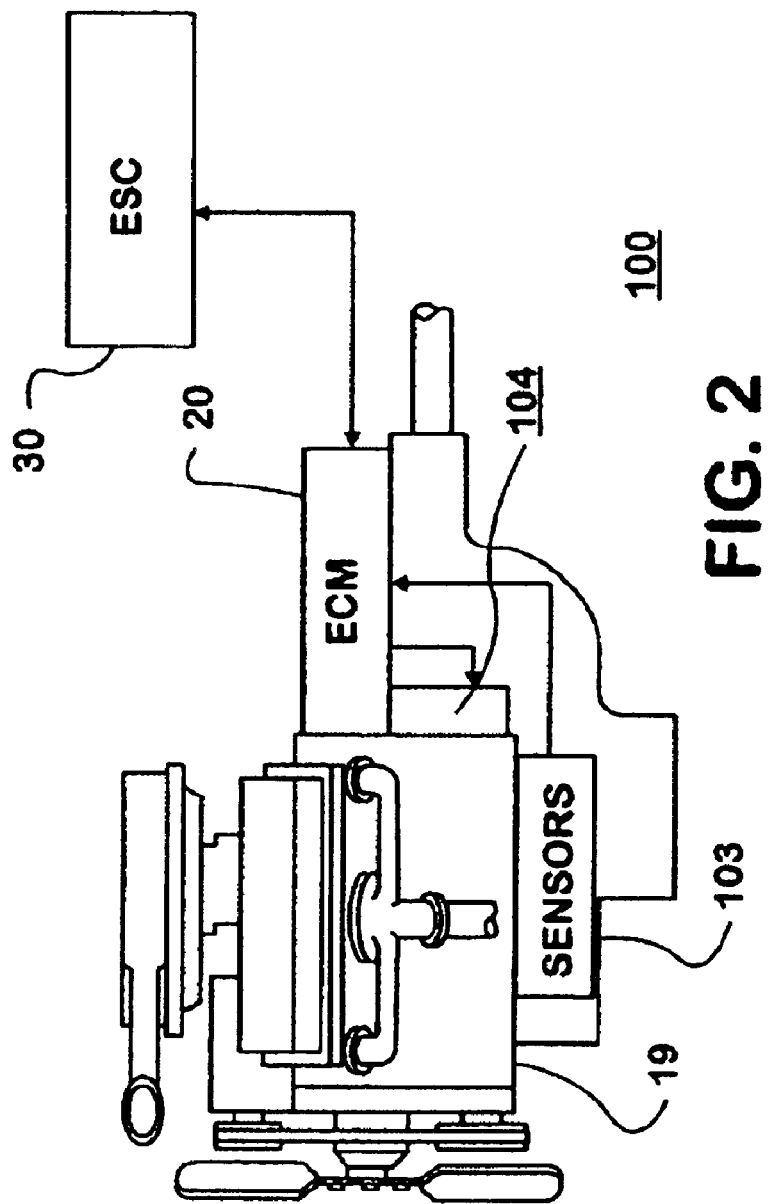
FIG. 2 is a block diagram of an engine control system.

FIG. 2 illustrates positioning of a group 103 of sensors and a group 104 of control actuators with respect to an engine 19. Engine 19 is preferably a diesel engine having a conventional internal lubricating oil circulation system and sump. Sensor group 103 includes a conventional package of sensors used with such engines. Sensor data is passed to an engine control module 20 which in turn communicates with ESC 30, which executes the estimation functions of the preferred embodiment of the invention.

Figure 3:
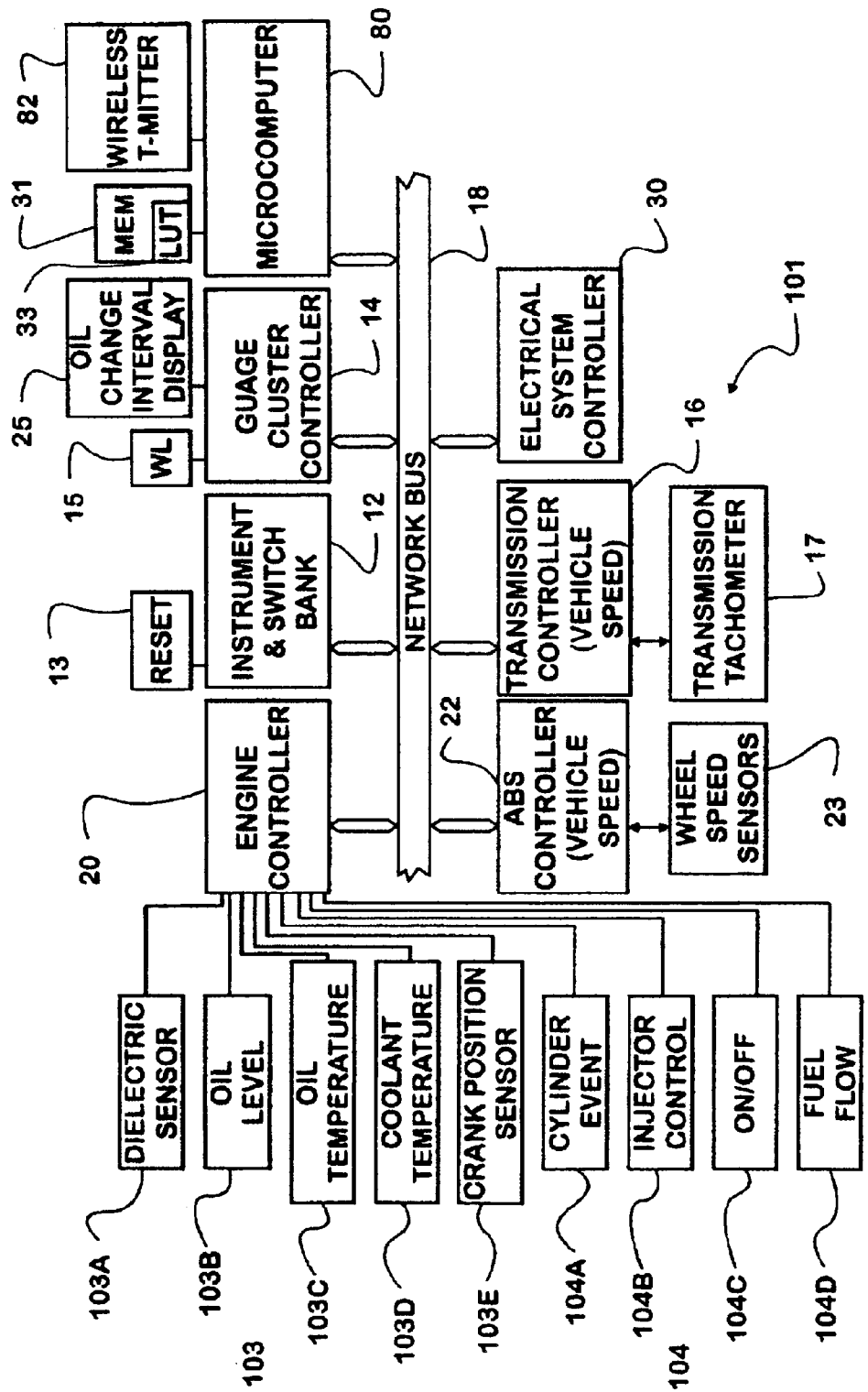
FIG. 3 is a block diagram of a controller area network for a vehicle.

FIG. 3 illustrates a vehicle controller area network (CAN) 101 including the possible local sources of data relating to implementation of an oil change algorithm and the local controllers to which oil change interval information and warnings are sent. Engine controller module 20, instrument and switch bank 12, gauge cluster 14, anti-lock brake system controller 22, transmission controller 16, on board microcomputer 80 and ESC 30 all communicate over network bus 18. ESC 30 is presumed to maintain a real time clock.

Engine controller module (ECM) 20, as already discussed, is the local controller which collects most of the required data. ECM 20 is connected to group 103 of engine sensors 103A-E, which include an oil dielectric sensor 103A, an oil level sensor 103B, an oil temperature sensor 103C, a coolant temperature sensor 103D and a crank position sensor 103E. Oil dielectric sensor 103A and oil level sensor 103B may be implemented as one device.

Control actuator group 104 includes controllers and counters for events under the control of ECM 20. An ON/OFF controller 104C indicates whether the engine 19 is running. ECM 20 will provide control signals to injector control 104B. Timing information for the injector control signals of course requires piston position information, which is typically derived from crankshaft position. This information comes from a crankshaft position sensor 103E. ECM 20 also has control over fuel flow 104D and a counter tracking cylinder ignition events 104A.

In the preferred embodiment of the estimation algorithm, a mileage estimate until an oil change is displayed to the operator. Accordingly, distances traveled must be recorded and rates of oil degradation with respect to the distance traveled determined. Vehicle odometer functions may be combined with a vehicle's anti-lock brake system (ABS) controller 22, which has wheel speed sensors 23 associated with each of the vehicle's wheels. Wheel speed signals may be combined to generate velocity and distance traveled data. Vehicle speed and distance traveled may alternatively be measured by a transmission output tachometer 17. The tachometer signal may be processed with transmission controller 16 by the engine controller 20, which receives the raw signal over bus 18.

Occurrence of an oil change is preferably noted by the operator using an oil change interval reset switch 13 coupled to instrument and switch bank 12. An engine lubricating oil condition warning light 15 and a distance indication readout 25 for oil change intervals are coupled to a gauge cluster controller 14.

An on board microcomputer 80 executes the oil change interval estimation algorithms of the present invention by access to a memory 31. The estimation algorithms are preferably implemented in one or more look up tables 33 stored in memory 31.

Figure 6:
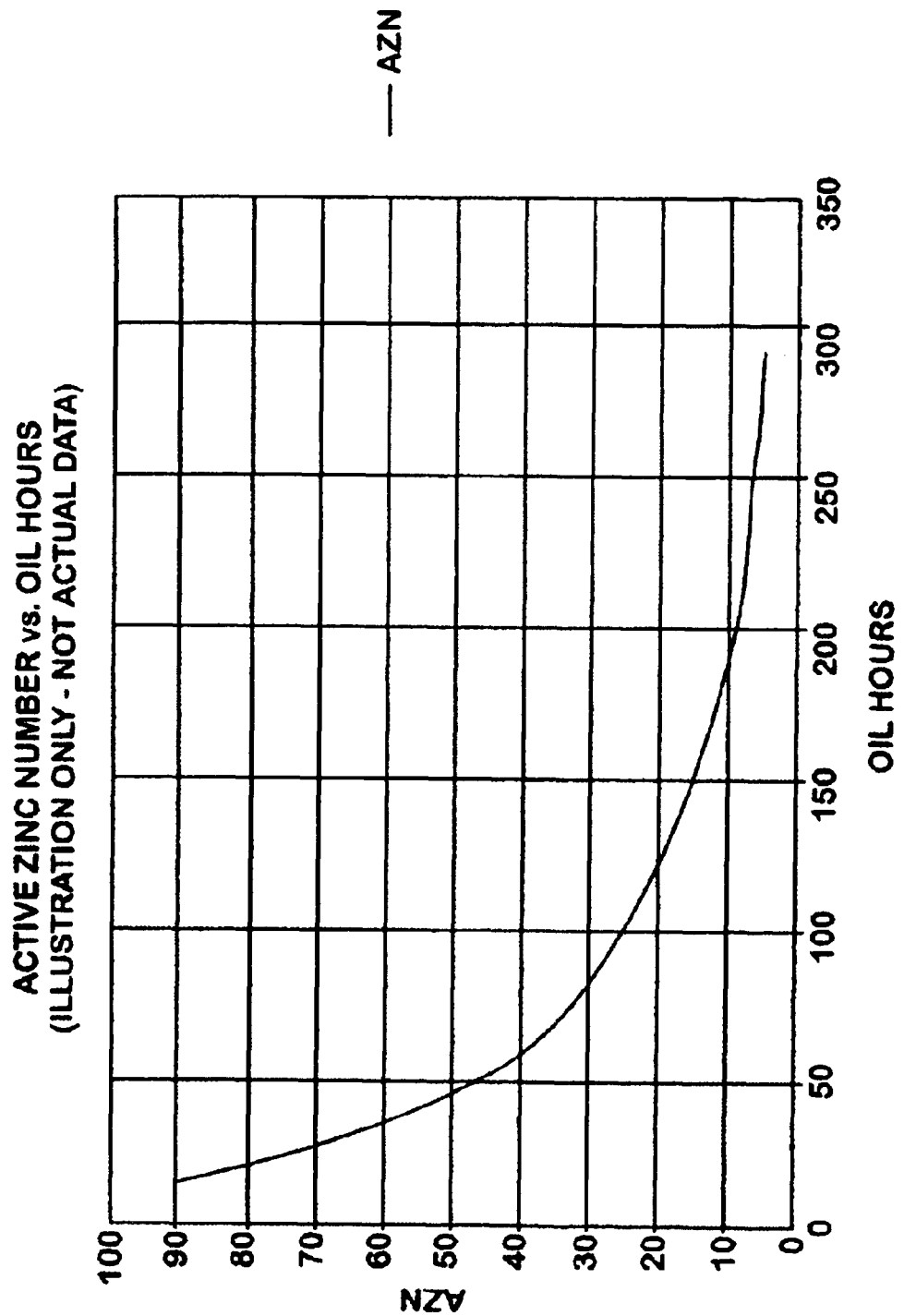
FIG. 6 is a graph illustrating decreasing active zinc against engine running time.

Prior art oil life estimation algorithms executed by on board vehicle or engine controllers have emphasized measuring oil TBN, soot level and viscosity against fixed limits, any one of which defines the limit of oil life. However, the minimum TBN allowable may vary depending upon circumstances, and, as long as TBN exceeds TAN, the oil retains a buffer against acid attack on engine components and can continue to be used, providing other oil characteristics are acceptable. The present invention, rather than measuring useful life of the oil against a prefixed limit TBN, measures TBN against TAN (see FIG. 5). TAN and TBN are not necessarily affected by engine operation in the same way all the time. TBN and TAN are therefore independently estimated to determine the limit of the oil's useful life. The point of intersection of TBN and TAN as illustrated in FIG. 5 is not necessarily the limit for TBN depletion, since different "oil equivalent hours" may accumulate for TBN and TAN over a given operating period. TBN is progressively depleted as a function of lubricating oil equivalent hours and TAN increases as a function of lubricating oil equivalent hours. TBN will eventually equal TAN with or without their lubricating oil equivalent hours being equal. An active zinc depletion limit (see FIG. 6) is provided as a supplemental minimum limit as the most likely secondary limit reached instead of the TBN=TAN limit. Shear in a lubricating oil may be defined as the degree of breakdown of the long chain molecules under mechanical action. The mechanical action is the operation of engine valves, valve lifters, fuel injection actuators, the oil pumps, sliding of pistons against cylinder walls, etc. Increasing shear is manifested by a loss of viscosity. Viscosity too is difficult to measure in situ, but is generally related to engine revolutions and power output for a specific engine type. The progressive depletion of AZN is related to the same factors allowing estimated viscosity to be correlated to AZN depletion.

Figure 4A:
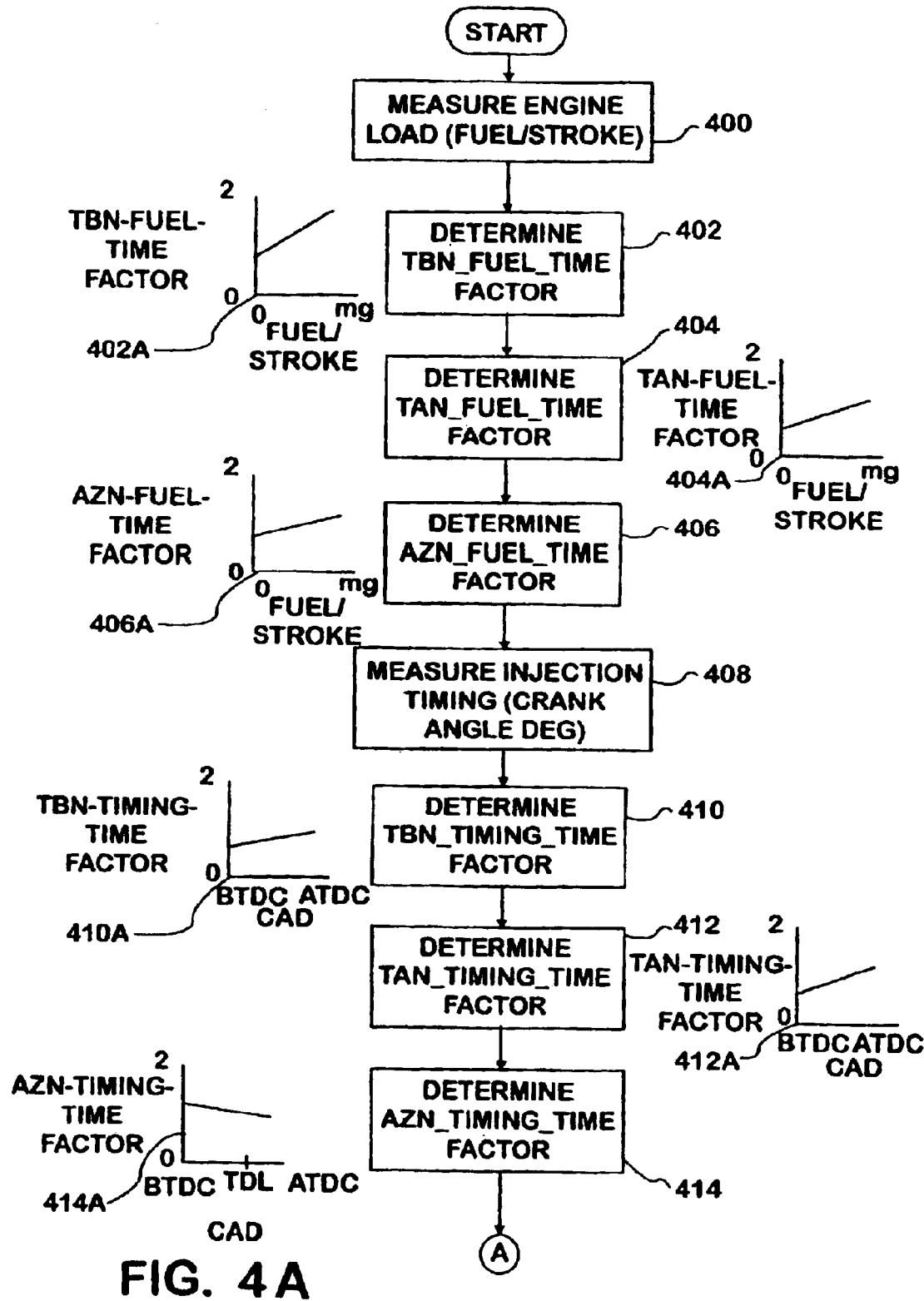
FIGS. 4A–C are sections of a single flow chart illustrating the method of the present invention for determining timing of engine oil changes.
Figure 4B:
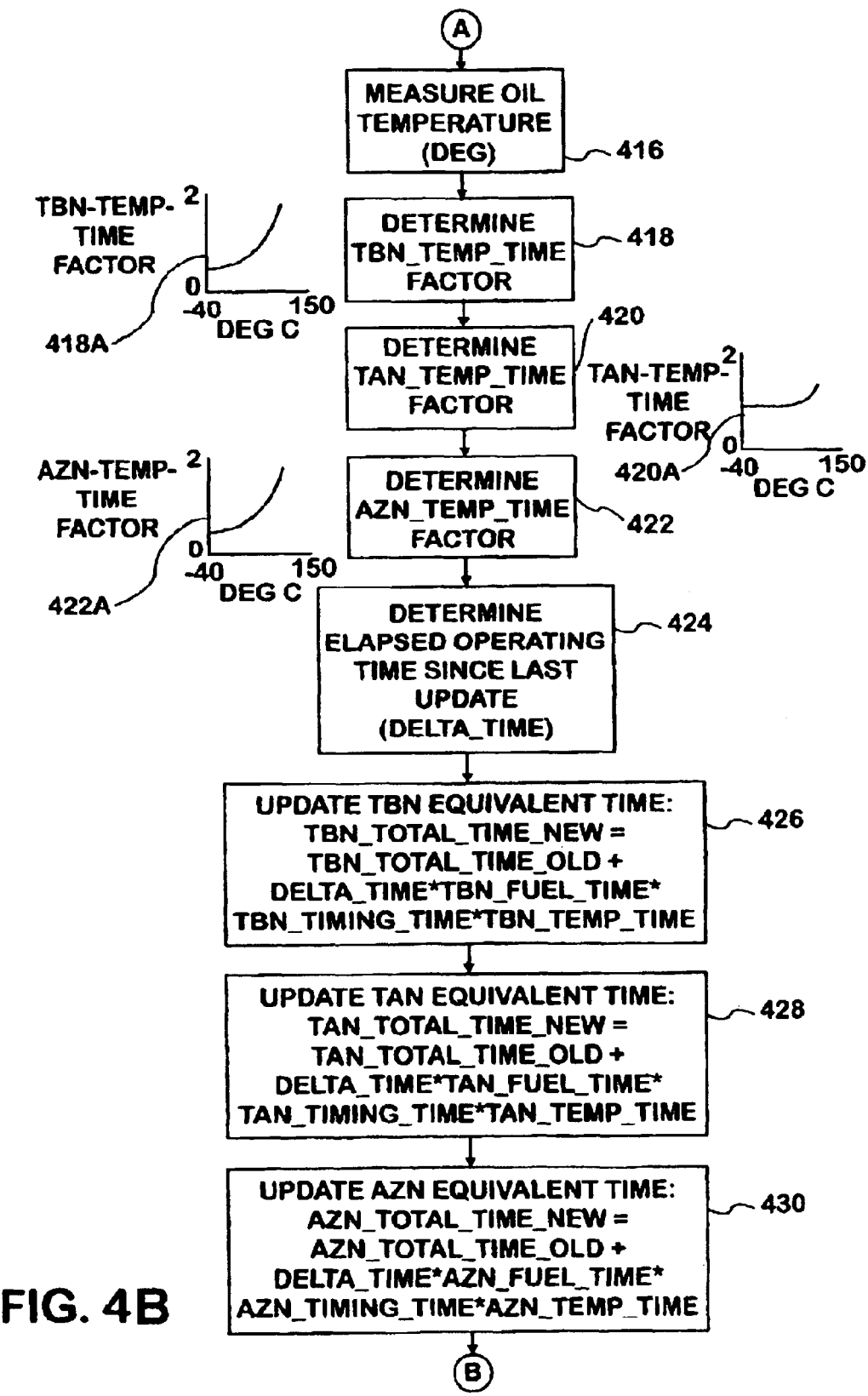
Figure 4C:
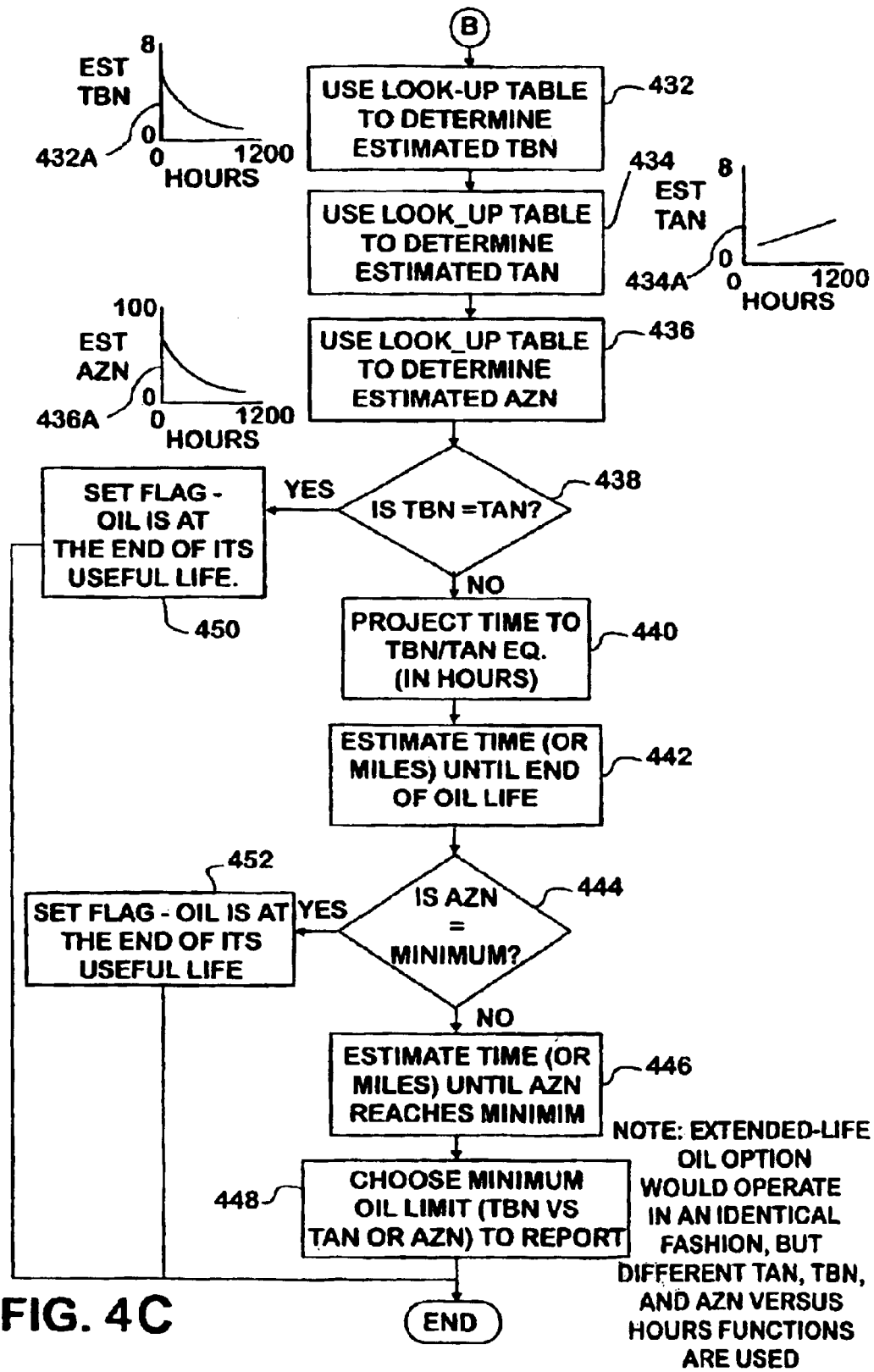

Referring now to FIG. 4, the algorithm providing an estimate of oil useful life is illustrated. The algorithm is periodically executed to take a sample of engine operating conditions. The results of all of the initial group of functions are normalized. The results are unitless ratios or factors. The functions are expressed in look up tables which were empirically developed. The depletion of TBN is primarily dependent upon engine load. Engine load is determined from the quantity of fuel burned per stroke and thereby the amount of sulfur transferred from the fuel to the lubricating oil. Accordingly, at step 400 a measurement of "engine load" in terms of its proxy, fuel per stroke, is taken. At step 402 a TBN_fuel_time factor for the TBN is retrieved from a look up table represent by functional graph 402A. Specific values for inputs are not given since the relationships are highly dependent on the engine configuration. The secondary input variables for the function are fuel flow, cylinder events and time which are used to calculate fuel used per piston stroke. Fuel/stroke is the direct input into the look up table represented by graph 402A and the output is a unitless "TBN_Fuel_Time_Factor" which is represented as a linearly increasing function per fuel per stroke. In other words, if engine load is heavier than normal, a given period of operation will be treated as though it were longer and if the load is light a given period will be treated as a shorter operating period.

Fuel used per stroke is also empirically related to additions to the TAN and depletion of the active zinc number (AZN). At step 404 a fuel_time factor for the TAN is retrieved from a look up represent by functional graph 404A. The output is a unitless "TAN_Fuel_Time_Factor" which is represented as a linearly increasing function of fuel per stroke indicating an increase in equivalent operating time. At step 406 a fuel_time factor for the AZN depletion is retrieved from a look up represent by functional graph 406A. The output is a unitless "AZN_Fuel_Time_Factor" which is represented as a linearly increasing function of fuel per stroke.

At step 408 injection timing (in terms of crank angle degrees) is determined from the engine position sensor signal and the injection timing commands from the ECM 20. Steps 410, 412 and 414 use timing to retrieve a TBN_Timing_Time_Factor, a TAN_Timing_Time_Factor and a AZN_Timing_Time_Factor. TBN depletion (function 410A) increases linearly with advances in timing (from before top dead center (BTDC) to after top dead center (ATDC) and accordingly the equivalent operating time is increased. Additions to the TAN are an increasing function (412A) of timing, meaning greater amounts of acid are added per unit time as injection timing is delayed. Equivalent operating time is increased for both the TAN and TBN with delays in injection timing. The amount of zinc depletion decreases with advances in timing (function 414A) meaning that delays in timing result in the period being treated as ever shorter equivalent operating times.

At step 416 oil temperature is measured. Steps 418, 420 and 422 use oil temperature to retrieve a TBN_Temp_Time_Factor, a TAN_Temp_Time_Factor and a AZN_Temp_Time_Factor. TBN depletion (function 418A) increases exponentially with increasing oil temperature. Similarly, additions to TAN are an exponentially increasing function (420A) of oil temperature. Zinc depletion per unit time also increases exponentially with increasing oil temperature (function 422A).

Finally, as the last preliminary step taken before updating the variables tracking TBN depletion, TAN addition and AZN depletion, the operating time that has elapsed since the last sample was taken is updated (referred to as delta_time) at step 424. In steps 426 through 430 Delta_time is multiplied by sets of related factors (e.g. the factors related to zinc depletion) developed in steps 400 through 422 to generate a change in "equivalent operating hours" to be added to the accumulated "equivalent operating hours" from earlier sample periods. The accumulated equivalent times for each oil property are then used as inputs into look tables 432A, 434A and 436A to find TBN, TAN and AZN. It should be noted again that the equivalent operating hours generated at steps 432, 434 and 436 for TBN, TAN and AZN may differ from one another.

Step 438 is the primary limiting step for oil life. The step provides for determining if TBN is equal (or less than) TAN, in which case the lubricating oil is indicated as reaching the end of useful life. The process is exited by the YES branch from step 438 to step 450, which provides for setting the appropriate flag, resulting in the appropriate warnings being given to the operator of the vehicle. If TBN is greater than TAN, the NO branch takes the process from step 438 to step 440, where a projection is made of the remaining useful life of the lubricating oil. This can be achieved by extrapolating current trends until TBN and TAN are projected to equal one another. This results in distinct projected numbers of TBN and TAN equivalent operating hours until TAN and TBN equal one another. At step 442 equivalent operating hours may be converted into conventional hours and multiplied by average speed to provide a mileage estimate until an oil change is required. The equivalent operating hours estimate which equates to the smallest actual operating hours figure is used to determine a limit distance estimate.

At step 444, following step 442, AZN is compared to its minimum limit. Upon reaching the limit, the YES branch from the step advances processing to step 452, which provides for setting a flag indicating the end of the oil's useful life. The appropriate indication is also made at this time to the operator. If AZN exceeds its minimum at step 444, step 446 is executed to develop an estimate of the time (or miles) until the limit is reached. Step 448 follows, where the lower estimate resulting from the comparison of TBN to TAN or of AZN to its limit is displayed to the operator as the distance to a required oil change.

The system can be made more robust by taking into account the possibility of loss of oil or intrusion of foreign material into the engine oil. These factors can become important where an engine is damaged or is subjected to unusual operating cycles. For example, if an engine is operated for short cycles, and does not reach or maintain normal operating temperatures, water which has found its way into the oil will not be forced from the oil by evaporation. Where water remains in the engine it provides a solvent for sulphur-hydrogen based compounds produced as a by product of combustion and escaping around the pistons from the combustion chambers. Water infiltration adversely affects lubrication as well. The model's robustness is improved by taking into account the temperature cycling of the engine oil. An approximation of the effect of the engine's temperature cycle is obtained by timing total engine operating time below a threshold temperature.

$$D(t)=d_0 t \qquad (3)$$

where t is the cumulative time below the temperature limit since the last oil change. Short operating cycles at low oil temperatures can be equated to higher equivalent operating times as done with the factors already treated.

Certain types of engine oil contamination may have less predictable effects, and may render any algorithm valueless. A failsafe real-time sensor such as a dielectric sensor used for measuring engine oil level may be used to detect the possible invasion of the oil by water or ethylene glycol. If the engine does not reach or maintain the threshold temperature, and the dielectric sensor indicates a high dielectric level, a problem is indicated. If a high dielectric coefficient is indicated and engine temperature is higher than the threshold limit, the presence of ethylene glycol is indicated and an alarm should be lit or sounded. Fuel contamination, and the consequent dilution and loss of viscosity of engine oil, can produce problems. In general, this may be caused by fuel injector malfunction and indicated by differential engine speed caused by cylinder to cylinder power imbalances. The crank position sensor signal can be used as an indicator of the possibility of this condition.

While the invention is shown in only one of its forms, it is not thus limited but is susceptible to various changes and modifications without departing from the spirit and scope of the invention.

What is claimed is:

1. A method of estimating the useful life of lubricating oil in an internal combustion engine, comprising the steps of:
   measuring variables relating to operation of the internal combustion engine;
   estimating a depletion rate for a TBN in the lubricating oil from the measured variables;
   estimating an accretion rate for a TAN in the lubricating oil from the measured variables; and
   determining a time span until the TBN and the TAN equal one another as an estimate of remaining useful life of the lubricating oil.

2. A method of estimating the useful life of lubricating oil as set forth in claim 1, wherein the internal combustion engine is installed on a motor vehicle, the method further comprising the step of:
   relating the determined time span to a distance and displaying the distance to an operator of the vehicle; and
   warning the operator when TBN and TAN equal one another.

3. A method of estimating the useful life of lubricating oil as set forth in claim 2, further comprising the step of:

estimating depletion of an active zinc number in the lubricating oil; and comparing the accumulated depletion of the active zinc number to a fixed minimum limit to determine a maximum limit of lubricating oil useful life.

4. A method of estimating the useful life of lubricating oil as set forth in claim 3, further comprising the steps of:

relating the maximum limit of lubricating oil useful life based on the active zinc number depletion rate to a distance; and setting the distance until the lubricating oil change to the lesser of the distance based on the accumulated depletion of the active zinc number and the determined time span and displaying the distance.

5. A method of estimating the useful life of lubricating oil as set forth in claim 4, wherein the steps of estimating the depletion of the TBN and the accretion of the TAN further comprise:

independently relating engine load, ignition timing and oil temperature to the depletion of the TBN and accretion rate of the TAN.

6. A method of estimating the useful life of lubricating oil as set forth in claim 5, the method further comprising the steps of:

equating a depletion rate for the TBN to a TBN equivalent operating hours factor;

equating an accretion rate for the TAN to a TAN equivalent operating hours factor;

providing a TBN look up table indexed by TBN equivalent operating hours;

providing a TAN look up table indexed by TAN equivalent operating hours;

using the TBN equivalent operating hours factor as an input to the TBN look up table to recover an estimated TBN; and using the TAN equivalent operating hours factor as an input to the TAN look up table to recover an estimated TAN.

7. A motor vehicle comprising:

an internal combustion engine having a lubricating system;

a lubricating oil temperature sensor;

an engine crankshaft position sensor;

a fuel injection means for setting fuel flow controller responsive to the engine crankshaft position sensor and the fuel flow;

lubricating oil for circulating in the lubricating system, the lubricating oil including buffers for neutralizing acid infiltration of the oil and metal salts for enhancing the lubricity of the oil; and data processing means programmed for equating oil temperature, fuel rates and ignition timing for estimating depletion of the buffers, accretion of acid, and depletion of the metal salts.

8. A motor vehicle as set forth in claim 7, further comprising:

a programming executable on the data processing means for expressing rates of buffer depletion and acid accretion to equivalent operating hours for each variable independently;

a look up table of buffer concentration indexed to equivalent operating hours for the buffer; and a look up table of acid concentration indexed to equivalent operating hours for the total acid.

9. A motor vehicle as set forth in claim 8, further comprising:

means for comparing the acid concentration and base concentration figures returned from the look up tables as an indication of end of lubricating oil useful life.

10. A motor vehicle as set forth in claim 9, further comprising:

means responsive to the base concentration exceeding the acid concentration for projecting an operating time duration until the base concentration and acid concentration are equal; and means for relating the projected operating duration to a distance for display.

11. A motor vehicle as set forth in claim 10, further comprising:

programming executable on the data processing means for equating oil temperature and engine operation in terms of fuel rates and ignition timing from the engine crankshaft position sensor and fuel injection controller for estimating depletion of the metal salts; and determining a projected operating endurance until depletion of the metal salts reaches a limit and comparing the projected operating duration to determine an oil change interval distance.

12. A motor vehicle as set forth in claim 10, further comprising:

memory accessible by the data processing means; and look up tables stored in memory and accessible to the programming executables to provide estimates of depletion of buffers and accretion of acids in the lubricating oils, indexed in terms of equivalent operating hours.

* * * * *